United States Patent
Yang et al.

(10) Patent No.: US 10,436,671 B2
(45) Date of Patent: Oct. 8, 2019

(54) SHOCK-RESISTANCE TESTING APPARATUS

(71) Applicants: Fu Tai Hua Industry (Shenzhen) Co., Ltd., Shenzhen (CN); HON HAI PRECISION INDUSTRY CO., LTD., New Taipei (TW)

(72) Inventors: Kang-Xian Yang, Shenzhen (CN); Ke-Rui Zeng, Shenzhen (CN); Kun-Jia Hsieh, New Taipei (TW); I-Cheng Huang, New Taipei (TW); Wen-Hsien Huang, New Taipei (TW)

(73) Assignees: Fu Tai Hua Industry (Shenzhen) Co., Ltd., Shenzhen (CN); HON HAI PRECISION INDUSTRY CO., LTD., New Taipei (TW)

(*) Notice: Subject to any disclaimer, the term of this patent is extended or adjusted under 35 U.S.C. 154(b) by 280 days.

(21) Appl. No.: 15/446,442

(22) Filed: Mar. 1, 2017

(65) Prior Publication Data

US 2017/0299461 A1    Oct. 19, 2017

(30) Foreign Application Priority Data

Apr. 13, 2016 (CN) .......................... 2016 1 0227595

(51) Int. Cl.
*G01M 7/08* (2006.01)
*G01N 3/303* (2006.01)

(52) U.S. Cl.
CPC .............. *G01M 7/08* (2013.01); *G01N 3/303* (2013.01); *G01N 2203/0037* (2013.01)

(58) Field of Classification Search
None
See application file for complete search history.

(56) References Cited

U.S. PATENT DOCUMENTS

| | | | | |
|---|---|---|---|---|
| 2,827,790 A * | 3/1958 | Brown | ................... | G01M 7/045 73/1.38 |
| 5,309,847 A * | 5/1994 | Matsumoto | .............. | B23Q 1/25 108/143 |
| 5,523,941 A * | 6/1996 | Burton | .................... | B23Q 1/623 269/73 |
| 5,613,403 A * | 3/1997 | Takei | ...................... | B23Q 1/621 108/143 |
| 5,724,893 A * | 3/1998 | Lee | .......................... | G01M 7/06 108/137 |
| 5,948,987 A * | 9/1999 | Liu | ........................ | G01M 7/045 73/432.1 |

(Continued)

*Primary Examiner* — Paul M. West
*Assistant Examiner* — Mark A Shabman
(74) *Attorney, Agent, or Firm* — ScienBiziP, P.C.

(57) ABSTRACT

A shock-resistance testing apparatus includes a support base, a first rotating component and a controller provided on the support base. A second rotating component is coupled to one side of the first rotating component. A testing board is placed on the first rotating component. A falling board is placed on the testing board. The controller controls the first rotating component to drive the second rotating component rotating from one side of the testing board to another side of the testing board. The controller controls the second rotating component to lift the testing board. The controller controls the second rotating component to move away from the testing board so that the testing board falls.

20 Claims, 3 Drawing Sheets

(56) References Cited

U.S. PATENT DOCUMENTS

| | | | | |
|---|---|---|---|---|
| 6,904,807 B1 * | 6/2005 | Butts | ................ | G01M 7/04 |
| | | | | 73/662 |
| 7,596,985 B2 * | 10/2009 | Ido | ................ | G01N 3/303 |
| | | | | 73/11.01 |
| 7,823,516 B2 * | 11/2010 | Yamazaki | ................ | B23Q 1/60 |
| | | | | 108/20 |
| 8,104,752 B2 * | 1/2012 | Eidelberg | ................ | G03B 27/58 |
| | | | | 108/140 |
| 8,453,491 B2 * | 6/2013 | Yu | ................ | G01M 7/08 |
| | | | | 33/613 |
| 8,516,877 B2 * | 8/2013 | Le | ................ | G01N 3/303 |
| | | | | 248/127 |
| 9,205,600 B1 * | 12/2015 | Kerr | ................ | B29C 64/20 |
| 9,395,400 B1 * | 7/2016 | Islam | ................ | G01R 31/04 |

* cited by examiner

SHOCK-RESISTANCE TESTING APPARATUS

FIELD

The subject matter herein generally relates to a shock-resistance testing apparatus.

BACKGROUND

Recently, there are more and more electronic devices (e.g., mobile phone, tablet, etc.) for personal use in the market. The electronic devices might fall to the ground when the user is not carefully using the electronic device. Therefore, the electronic device must have capability of shock-resistance to decrease the impact from external force. Traditionally, a shock-resistance testing apparatus is able to test one direction of electronic device. However, when the electronic device falls, the impact on the electronic devices may be generated in different directions. Therefore, the shock-resistance testing apparatus should provide functions for testing impact on different directions of the electronic device.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Implementations of the present technology will now be described, by way of example only, with reference to the attached figures.

DETAILED DESCRIPTION

Figure 1:
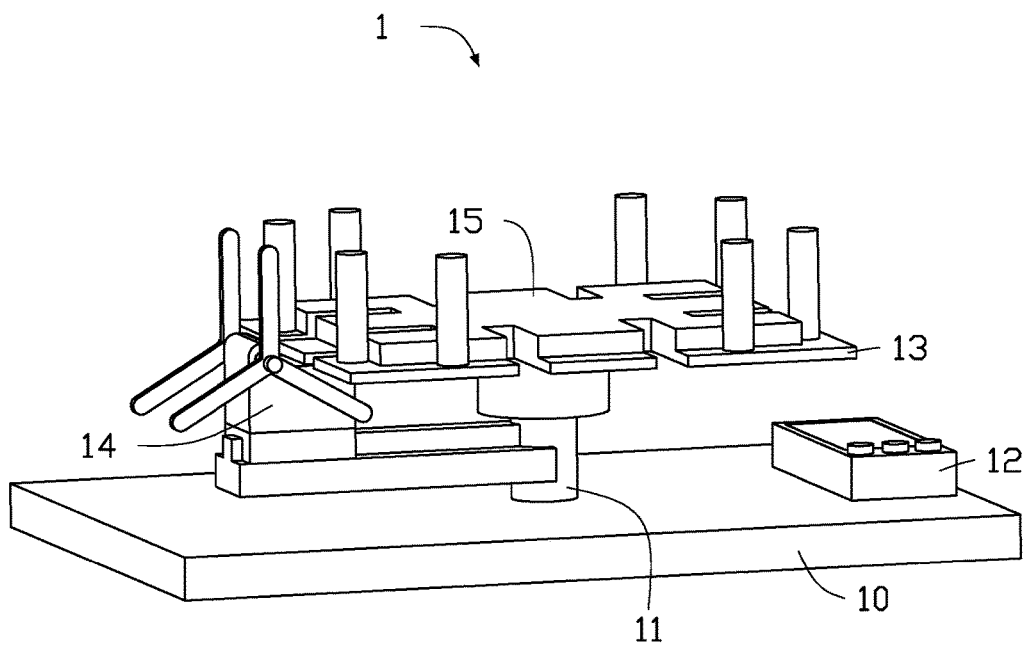
FIG. 1 is a schematic view illustrating an exemplary embodiment of a shock-resistance testing apparatus.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

Definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "comprising," when utilized, means "including, but not necessarily limited to"; it specifically indicates open-ended inclusion or membership in the so-described combination, group, series and the like.

The present disclosure relates to a shock-resistance testing apparatus. A shock-resistance testing apparatus includes a support base, a first rotating component and a controller provided on the support base. A second rotating component is coupled to the one side of the first rotating component. A testing board is provided on the first rotating component. A falling board is provided on the testing board. The controller is configured to control the first rotating component to drive the second rotating component rotating from one side of the testing board to another side of the testing board. The controller is configured to control the second rotating component to lift the testing board. The controller is configured to control the second rotating component to move away from the testing board so that the testing board falls down.

FIG. 1 is a view of an exemplary embodiment of a shock-resistance testing apparatus 1 of this disclosure. The shock-resistance testing apparatus 1, comprises a support base 10 having a first rotating component 11 and a controller 12. A testing board 13 is coupled to a top surface the first rotating component 11. A second rotating component 14 is coupled to one side of the first rotating component 11 and a falling board 15 is put on the testing board 13.

Figure 2:
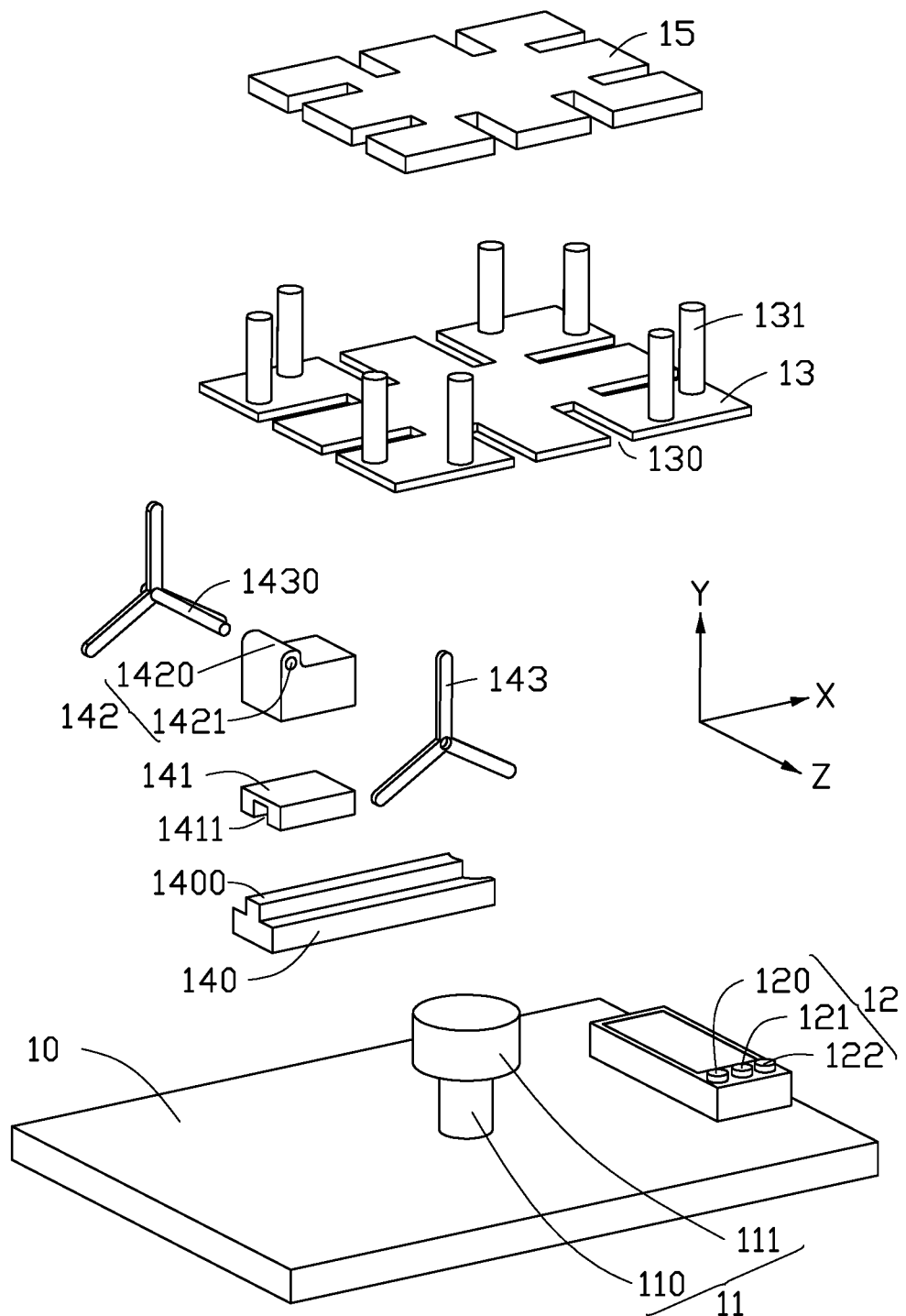
FIG. 2 is an exploded view of the shock-resistance testing apparatus of FIG. 1.
Figure 3:
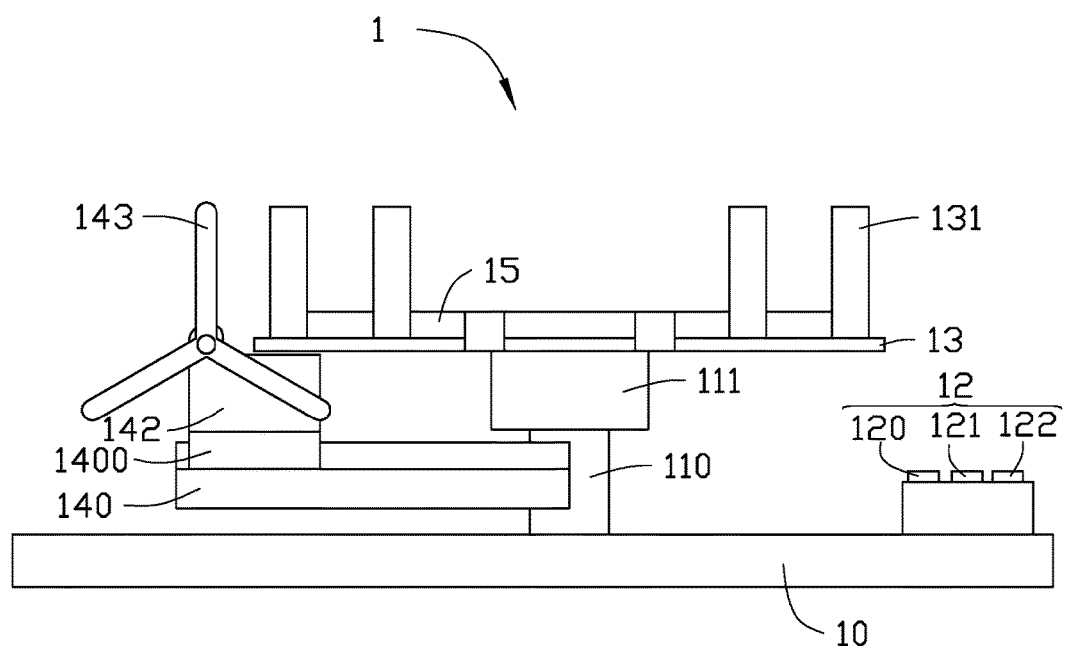
FIG. 3 is a planar view of the shock-resistance testing apparatus of FIG. 1.

FIG. 2 is an exploded view of the shock-resistance testing apparatus 1 of this disclosure (refer to FIG. 3 as a planar view of the shock-resistance testing apparatus of FIG. 1). The first rotating component 11 comprises a supporting post 110 and a spacer plate 111 provided on the supporting post 110. In some exemplary embodiments, the supporting post 110 and the spacer plate 111 are cylinders. When the supporting post 110 rotates, the spacer plate 111 does not rotates. In this exemplary embodiment, the supporting post 110 rotates about a Y-axis, and the Y-axis is perpendicular to the direction of the support base 10.

The testing board 13 has at least one notch 130. In this exemplary embodiment, the testing board 13 is substantially rectangular. Every side of the testing board 13 has two notches 130. The shape of the falling board 15 is similar to the testing board 13 but is slightly smaller than the testing board 13. The falling board 15 is configured to receive the electronic device for the test.

In some exemplary embodiments, the testing board 13 comprises at least one spacer post 131. The spacer post 131 is provided near an edge of the testing board 13. In this exemplary embodiment, two spacer posts 131 are provided on each edge of the testing board 13. Eight spacer posts 131 are placed around to the falling board 15 according to the exemplary embodiment in FIG. 1. The electronic device is placed on the falling board 15 without falling off from the edges of the testing board 13 because the spacer posts 131 are able to obstruct the electronic device from moving off the falling board. In some exemplary embodiments, the positions of the spacer posts 131 can be adjusted based on the size of the electronic device.

The second rotating component 14 comprises a linear guideway 140, a sliding block 141, a supporting part 142 and at least one baffle part 143. In some exemplary embodiments, the linear guideway 140 comprises a protrusion block 1400.

A slidable groove 1411 is provided on a top side of the sliding block 141. The protrusion block 1400 is configured to be placed in the slidable groove 1411 so that the sliding block 141 is able to slide along the slidable groove 1411 linearly.

The supporting part 142 is mounted on a top surface of the sliding block 141 away from the linear guideway 140. When the sliding block 141 slides along the linear guideway 140, the baffle part 143 moves with the sliding block 141. Then the supporting part 142 moves away or near the first rotating component 11.

In this exemplary embodiment, the supporting part 142 has a protrusion portion 1420. The protrusion portion 1420 has a hole 1421.

At least one baffle part 143 coupled to one side of a cross bar 1430, and the cross bar 1430 is installed to pass through the hole 1421. The baffle bars 143 is inserted in the notches 130 of the testing board 13.

In some exemplary embodiments, the number of the baffle part 143 is two for rotating together. Each baffle part 143 is coupled to the cross bar 1430. Each baffle part 143 is inserted in the notch 130 of the testing board 13. In some exemplary embodiments, the baffle part 143 can be one-armed, three-armed or multiple-armed structures. When the baffle part 143 is coupled to the cross bar 1430 installed through the hole 1421, the baffle part 143 is able to rotate. When the baffle part 143 touches the testing board 13, the testing board 13 is lifted up.

In some exemplary embodiments, the shock-resistance testing apparatus 1 further comprises a first motor drive, a second motor drive and a third motor drive (the motor drives are not shown). The first motor drive is installed inside the supporting post 110 so that the first motor drive is configured to drive the supporting post 110 to rotate around an axis, such as Y axis (shown in FIG. 2). The second motor drive is installed inside the sliding block 141 so that the second motor drive is configured to drive the sliding block to move along the linear guideway 140. The third motor drive is installed inside the supporting part 142 so that the third motor drive is configured to drive the baffle part 143 to rotate about the cross bar 1430 in order to lift the testing board 13.

In some exemplary embodiments, the controller 12 comprises a first control module 120, a second control module 121, and a third control module 122. The first control module 120 is coupled to a first wireless communication unit to control the first motor drive. The second control module 121 is coupled to a second wireless communication unit to control the second motor drive. The third control module 122 is coupled to a third wireless communication unit to control the first motor drive In some exemplary embodiments, the first control module 120 is electrically connected to the first motor drive. The second control module 121 is electrically connected to the second motor drive. The third control module 122 is electrically connected to the third motor drive.

An exemplary operation of the shock-resistance testing is described as follow:

The first control module 120 of the controller 12 resets the shock-resistance testing apparatus 1 to an original condition. The original condition is the condition that the first motor drive drives the supporting post 110, which is controlled by the first control module 120, to rotate about the Y axis. The baffle part 143 is configured to aim towards the notch 130 of the testing board 13. The Y axis is perpendicular to the support base 10.

The second control module 121 controls the second motor drive to drive the sliding block 141 to move to a first predetermined distance along the linear guideway 140 so that the baffle part 143 moves closer to the testing board 13. When the baffle part 143 rotates about the cross bar 1430, the testing board 13 can be lifted by the baffle part 143.

The third control module 122 controls the third motor drive to drive the baffle part 143 to rotate about the cross bar 1430. The testing board is lifted to a first predetermined height by the baffle part 143.

The second control module 121 controls the second motor drive to drive the sliding block 141 to move to a second predetermined distance along the linear guideway 140 so that the baffle part 143 moves away from the testing board 13. When the baffle part 143 moves away from the testing board 13, an electronic device placed on the testing board 13 falls to a second predetermined height. Because the electronic device is dropped from the first predetermined height to the second predetermined height, the shock-resistance testing on the electronic device is provided.

After the shock-resistance testing process, the first control module 120 controls the first motor drive to drive the supporting post 110 to rotate about the Y axis so that the baffle part 143 rotates from one side of the testing board 13 to another side of the testing board 13. When the baffle part 143 is configured to aim towards the notch 130 of the other side of the testing board 13, the next round of the shock-resistance testing begins. According to this shock-resistance testing process, the shock-resistance testing apparatus 1 is able to test the shock-resistance of different edges of the electronic device on the testing board 13.

In some exemplary embodiments, a control program is embedded in the controller 12. When a user starts the program, the controller 12 operates the shock-resistance testing apparatus 1 automatically without any users involved during the testing process.

In some exemplary embodiments, the testing board 13 is flexibly coupled to the spacer plate 111. The testing board 13 and falling board 15 both have notch 130 so that the testing board 13 and falling board 15 can be lifted by the baffle part 143 at the same time.

In some exemplary embodiments, the testing board 13 is securely placed at the spacer plate 111. The notch 130 of the testing board 13 is larger than the notch 130 of the falling board 15 so that the baffle part 143 is able to pass through the testing board 13 and only lifts the falling board 13.

In some exemplary embodiments, the testing board 13 is securely placed at the spacer plate 111. The falling board 15 has no notch on each edge of the falling board 15.

Some testing systems may comprise a shock-resistance testing apparatus and more than one testing apparatus. For instance, a testing system is integrated with a shock-resistance testing apparatus and an antenna testing apparatus. The testing system is not only used for testing shock-resistance but also for testing antenna features on an electronic device.

The exemplary embodiments shown and described above are only examples. Many details are often found in the art such as the other features of a shock-resistance testing apparatus. Therefore, many such details are neither shown nor described. Even though numerous characteristics and advantages of the present technology have been set forth in the foregoing description, together with details of the configuration and function of the present disclosure, the disclosure is illustrative only, and changes may be made in the details, including in matters of shape, size, and arrangement of the parts within the principles of the present disclosure, up to and including the full extent established by the board general meaning of the terms used in the claims. It will therefore be appreciated that the exemplary embodiments described above may be modified within the scope of the claims.

What is claimed is:

1. A shock-resistance testing apparatus, comprising:
a support base;
a first rotating component and a controller placed on the support base;
a second rotating component coupled to one side of the first rotating component;
a testing board placed on the first rotating component; and
a falling board placed on the testing board,
wherein the controller is configured to control the first rotating component to drive the second rotating component to rotate from one side of the testing board to another side of the testing board, and control the second rotating component to move near the testing board to lift the testing board and move away from the testing board so that the testing board falls.

2. The shock-resistance testing apparatus of claim 1, wherein the first rotating component comprises a supporting post and a spacer plate on the supporting post, the shock-resistance testing apparatus further comprises a first motor drive controlled by the controller to drive the supporting post such that the second rotating component is rotated from one side of the testing board to another side of the testing board.

3. The shock-resistance testing apparatus of claim 2, wherein the second rotating component comprises a linear guideway coupled to the supporting post, a sliding block coupled to the linear guideway, a supporting part coupled to the sliding block, and a baffle part coupled to the supporting part.

4. The shock-resistance testing apparatus of claim 3, wherein one side of the sliding block includes a slidable groove, the linear guideway comprises a protrusion block, and the protrusion block is placed in the slidable groove so that the sliding block is able to slide along the groove linearly.

5. The shock-resistance testing apparatus of claim 4, further comprises a second motor drive, wherein the second motor drive is configured to drive the sliding block to move along the linear guideway, such that the baffle part moves closer to the testing board or moves away from the testing board.

6. The shock-resistance testing apparatus of claim 5, wherein the controller comprises a second control module, and a third control module, and the second control module is configured to control the second motor drive.

7. The shock-resistance testing apparatus of claim 5, wherein the second motor drive is inside the sliding block.

8. The shock-resistance testing apparatus of claim 3, wherein the supporting part comprises a protrusion portion having a hole, a cross bar is passed through the hole, and the baffle bar is coupled to one side of the cross bar.

9. The shock-resistance testing apparatus of claim 8, further comprises a third motor drive, wherein the third motor drive is configured to drive the baffle part to rotate about the cross bar and to lift the testing board when the second rotating component is moved near the testing board.

10. The shock-resistance testing apparatus of claim 9, wherein the testing board comprises at least one notch at each side of the testing board, and at least one notch at each side of the falling board.

11. The shock-resistance testing apparatus of claim 10, wherein the testing board comprises at least one spacer post at each edge of the testing board, the edges are not edges of the notches.

12. The shock-resistance testing apparatus of claim 11, wherein the testing board is located on the spacer plate, the notch of the testing board is larger than the notch of the falling board, so that the baffle part is able to pass through the testing board and lift the falling board.

13. The shock-resistance testing apparatus of claim 9, wherein the controller comprises a third control module, and the third control module is configured to control the first motor drive.

14. The shock-resistance testing apparatus of claim 9, the third motor drive is inside the supporting part.

15. The shock-resistance testing apparatus of claim 3, wherein the baffle part is a pair of one-armed or multiple-armed structures.

16. The shock-resistance testing apparatus of claim 2, wherein the controller comprises a first control module, and the first control module is configured to control the first motor drive.

17. The shock-resistance testing apparatus of claim 2, wherein the first motor drive is inside the supporting post.

18. A testing system, comprising a shock-resistance testing apparatus and an antenna testing apparatus, wherein the shock-resistance testing apparatus comprising:
a support base;
a first rotating component and a controller placed on the support base;
a second rotating component coupled to one side of the first rotating component;
a testing board placed on the first rotating component; and
a falling board placed on the testing board,
wherein the controller is configured to control the first rotating component to drive the second rotating component to rotate from one side of the testing board to another side of the testing board, and control the second rotating component to move near the testing board to lift the testing board and move away from the testing board so that the testing board falls.

19. The testing system of claim 18, wherein the first rotating component comprises a supporting post and a spacer plate on the supporting post, the shock-resistance testing apparatus further comprises a first motor drive controlled by the controller to drive the supporting post such that the second rotating component is rotated from one side of the testing board to another side of the rotating board.

20. The testing system of claim 19, wherein the second rotating component comprises a linear guideway coupled to the supporting post, a sliding block coupled to the linear guideway, a supporting part coupled to the sliding block, and a baffle part coupled to the supporting part.

* * * * *